United States Patent
Galvez et al.

(10) Patent No.: US 12,311,008 B2
(45) Date of Patent: May 27, 2025

(54) PRODUCTS AND METHODS USING LUNASIN-ENRICHED SOY EXTRACT MIXTURES TO REDUCE FREE FATTY ACID LEVELS, INCREASE LEPTIN LEVELS AND INCREASE ADIPONECTIN LEVELS IN PLASMA

(71) Applicant: SL Technology, Inc., Chesterfield, MO (US)

(72) Inventors: Alfredo Flores Galvez, Folsom, CA (US); Ryan Schmidt, Chesterfield, MO (US); Carl Hastings, Chesterfield, MO (US)

(73) Assignee: SL Technology, Inc., Chesterfield, MO (US)

( * ) Notice: Subject to any disclaimer, the term of this patent is extended or adjusted under 35 U.S.C. 154(b) by 0 days.

(21) Appl. No.: 18/634,887

(22) Filed: Apr. 13, 2024

(65) Prior Publication Data

US 2024/0261368 A1 Aug. 8, 2024

Related U.S. Application Data

(63) Continuation of application No. 17/369,855, filed on Jul. 7, 2021, now Pat. No. 11,986,510, which is a continuation of application No. 16/297,680, filed on Mar. 10, 2019, now Pat. No. 11,096,984, which is a continuation of application No. 14/775,724, filed as application No. PCT/US2014/029753 on Mar. 14, 2014, now abandoned.

(60) Provisional application No. 61/852,101, filed on Mar. 15, 2013.

(51) Int. Cl.
| | |
|---|---|
| *A61K 38/16* | (2006.01) |
| *A23L 33/105* | (2016.01) |
| *A23L 33/18* | (2016.01) |
| *A61K 31/353* | (2006.01) |
| *A61K 36/03* | (2006.01) |
| *A61K 36/064* | (2006.01) |
| *A61K 36/10* | (2006.01) |
| *A61K 36/48* | (2006.01) |
| *A61K 36/484* | (2006.01) |
| *A61K 36/52* | (2006.01) |
| *A61K 36/67* | (2006.01) |
| *A61K 36/708* | (2006.01) |
| *A61K 36/738* | (2006.01) |
| *A61K 36/8962* | (2006.01) |

(52) U.S. Cl.
CPC .......... *A61K 38/168* (2013.01); *A23L 33/105* (2016.08); *A23L 33/18* (2016.08); *A61K 31/353* (2013.01); *A61K 36/03* (2013.01); *A61K 36/064* (2013.01); *A61K 36/10* (2013.01); *A61K 36/48* (2013.01); *A61K 36/484* (2013.01); *A61K 36/52* (2013.01); *A61K 36/67* (2013.01); *A61K 36/708* (2013.01); *A61K 36/738* (2013.01); *A61K 36/8962* (2013.01); *A23V 2002/00* (2013.01)

(58) Field of Classification Search
CPC ............ A61K 36/8962; A61K 2300/00; A61K 36/10; A61K 36/52; A61K 36/738; A61K 36/67; A61K 36/708; A61K 36/484; A61K 36/03; A61K 36/064; A61K 36/48; A61K 31/353; A23L 33/18; A23L 33/105; A23V 2002/00
USPC ...................................... 424/93.51
See application file for complete search history.

(56) References Cited

PUBLICATIONS

New Hope, Engredea News and Analysis, GlucAffect now includes LunaRich soy powder, Jun. 8, 2012, Available Online at: www.newhope.com/supply-news-amp-analysis/glucaffect-now-includes-lunarich-soy-powder.*
Cision PR Newswire Association, 3 Reasons to Fall in Love with Soy for American Heart Month, PR Newswire Association LLC, Published Feb. 17, 2012.*
Reliv GlucAffect, GlucAffect with LunaRich, Supplement Facts, Available Online at: reliv-static.s3-US-west-2.amazonaws.com/art/WebStuff/NutritionalPanels/US/ Glucaffect/Glucaffect-web.pdf, Dated Nov. 2017.*
Li et al., Serum leptin is associated with cardiometabolic risk and predicts metabolic syndrome in Taiwanese adults, Cardiovascular Diabetology, vol. 10, No. 36, (2011), pp. 1-8.*
Qian et al., Serum leptin, cholesterol and blood glucose levels in diabetics following a yoga and diet change program, Med Sci Monit, (2010), 16(1): pp. LE4-LE5.*

* cited by examiner

*Primary Examiner* — Jennifer M. H. Tichy
(74) *Attorney, Agent, or Firm* — Kathryn P. Wilke

(57) ABSTRACT

This invention relates generally to products and methods using lunasin-enriched soy extract combined with Reliv Now® to reduce free fatty acid levels and increase leptin levels and adiponectin levels in plasma for the control of obesity, type 2 diabetes and metabolic syndrome. More specifically, the present invention relates to novel compositions comprising lunasin enriched soy extract and Reliv Now® formulations, methods of using these compositions in individuals for the control of obesity, type 2 diabetes and metabolic syndrome, and methods of making compositions comprising them.

21 Claims, 6 Drawing Sheets

UnTrt   Temp (-)   A       B       C       D       E       F

A = LES
B = LES + SF
C = LES + SF digested
D = LES digested
E = Soy Protein Isolate digested
F = Soy Concentrate digested

PRODUCTS AND METHODS USING LUNASIN-ENRICHED SOY EXTRACT MIXTURES TO REDUCE FREE FATTY ACID LEVELS, INCREASE LEPTIN LEVELS AND INCREASE ADIPONECTIN LEVELS IN PLASMA

FIELD OF THE INVENTION

This invention relates generally to products and methods using lunasin-enriched soy extract combined with Reliv Now© formulation to reduce free fatty acid (FFA) levels and increase leptin levels and adiponectin levels in plasma in individuals for the control of obesity, type 2 diabetes and metabolic syndrome. More specifically, the present invention relates to novel compositions comprising lunasin enriched soy extract and Reliv Now® formulations, methods of using these compositions in individuals for the control of obesity, type 2 diabetes and metabolic syndrome, and methods of making compositions comprising them.

BACKGROUND OF THE INVENTION

According to the US Centers for Disease Control there is a rising trend in obesity levels today with one third of adults considered obese. Rates of type 2 diabetes have also increased markedly over the last 50 years in parallel with obesity. As of 2010, there were 285 million people in the US with type 2 diabetes. Long term complications from high blood glucose can include, without limitation, heart disease, strokes, diabetic retinopathy, kidney failure, and poor circulation of the limbs. Annual medical expenditures attributable to obesity have doubled in less than a decade, and are now as high as $147 billion per year. There is an obvious need for low cost, effective treatments to control obesity and type 2 diabetes.

There exists a need for improved compositions and related methods for effectively reducing free fatty acid levels, increasing leptin and adiponectin levels in plasma. The present invention provides these and other related benefits.

Definitions

To facilitate an understanding of the invention, a number of terms and phrases are defined below. Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The general techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

As used herein, the singular form "a", "an", and "the" includes plural references unless indicated otherwise. For example, "a" protease enzyme inhibitor includes one or more protease enzyme inhibitors.

As used herein "ug" is an abbreviation for microgram and "uM" is an abbreviation for micromole.

As used herein, "biological activity" and "bioactivity" refer to the in vivo activities of a compound or physiological responses that result upon in vivo administration of a compound, composition, or other mixture. Biological activity, thus, encompasses therapeutic effects and pharmaceutical activity of such compounds, compositions and mixtures. Biological activities may be observed and measured in in vitro systems designed to test or use such activities also.

As used herein, the term "biologically active" refers to a molecule having structural, regulatory and or biochemical functions of a naturally occurring lunasin molecule.

As used herein, the terms "disease" "disorder" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors.

As used herein, the term "effective amount" refers to the amount of a composition (e.g., comprising Lunasin) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs) and/or to direct, instruct, or advise the use of the composition for any purpose (preferably, for a purpose described herein). Where the administration of one or more of the present compositions is directed, instructed or advised, such direction may be that which instructs and/or informs the user that use of the composition may and/or will provide one or more of the benefits described herein.

Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

Administration which is directed may comprise, for example, oral direction (e.g., through oral instruction from, for example, a physician, health professional, sales professional or organization, and/or radio or television media (i.e., advertisement) or written direction (e.g., through written direction from, for example, a physician or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" includes through words, pictures, symbols, and/or other visible descriptors. Such direction need not utilize the actual words used herein, but rather use of words, pictures, symbols, and the like conveying the same or similar meaning are contemplated within the scope of this invention.

As used herein, the terms "co-administration" and "co-administering" refer to the administration of at least two agent(s) (e.g., composition comprising Lunasin and one or more other agents—e.g., Reliv Now®) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., heart disease). A composition which causes an improvement in any parameter associated with disease when used in the screening methods of the instant invention may thereby be identified as a therapeutic composition. The term "treatment" refers to both therapeutic treatment and prophylactic or preventative measures. For example, those who may benefit from treatment with compositions and methods of the present invention include those already with a disease and/or disorder (e.g., elevated cholesterol levels) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the terms "individual," "host," "subject" and "patient" refer to any animal, including but not limited to, human and non-human animals (for example, without limitation, primates, dogs, cats, pigs, cows, horses, sheep, rodents, poultry, fish, crustaceans, etc.) that is studied, analyzed, tested, diagnosed or treated. As used herein, the terms "individual," "host," "subject" and "patient" are used interchangeably, unless indicated otherwise.

As used herein, the term "antibody" (or "antibodies") refers to any immunoglobulin that binds specifically to an antigenic determinant, and specifically binds to proteins identical or structurally related to the antigenic determinant that stimulated their production. Thus, antibodies can be useful in assays to detect the antigen that stimulated their production. Monoclonal antibodies are derived from a single clone of B lymphocytes (i.e., B cells), and are generally homogeneous in structure and antigen specificity. Polyclonal antibodies originate from many different clones of antibody-producing cells, and thus are heterogenous in their structure and epitope specificity, but all recognize the same antigen. Also, it is intended that the term "antibody" encompass any immunoglobulin (e.g., IgG, IgM, IgA, IgE, IgD, etc.) obtained from any source (e.g., humans, rodents, non-human primates, lagomorphs, caprines, bovines, equines, ovines, etc.).

As used herein, the term "antigen" is used in reference to any substance that is capable of being recognized by an antibody.

As used herein, the terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody that specifically binds the primary antibody. The secondary antibody is typically conjugated to an enzyme that permits visualization of the antigen-antibody complex by the production of a colored reaction product or catalyzes a luminescent enzymatic reaction (e.g., the ECL reagent, Amersham).

The term "compound" refers to any chemical entity, pharmaceutical, drug, and the like that can be used to treat or prevent a disease, illness, sickness, or disorder of bodily function. Compounds comprise both known and potential therapeutic compounds. Compounds comprise polypeptides such as those described herein.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., Lunasin) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein "lunasin" refers to the natural, synthetically or recombinantly obtained soybean lunasin polypeptide. Detailed description of the Lunasin peptide and an evaluation of various functionally equivalent fragments and analogues appear in U.S. Pat. Nos. 6,107,287, 6,544,956, US Patent Application 2003/0229038, filed Nov. 22, 2002, U.S. Pat. No. 6,391,848, U.S. patent application Ser. No. 10/252,256, filed Sep. 23, 2002, U.S. patent application Ser. No. 10/302,633, filed Nov. 22, 2002, U.S. Pat. No. 7,731,995 and U.S. patent application Ser. No. 12/441,384, filed Mar. 14, 2009, all of which are hereby incorporated by reference herein in their entirety for all purposes.

As used herein "lunasin enriched" refers to compositions containing biologically active levels of naturally occurring lunasin, or a naturally occurring analogue of lunasin, that is at a concentration greater than that at which lunasin is found in the material used as the source of that lunasin or analogue.

As used herein "lunasin enriched soy extract" refers to compositions containing biologically active levels of naturally occurring lunasin that is at a concentration at least twice than that at which lunasin is naturally found in the source seed. Without limiting the invention to any particular source of the compositions of the present invention, lunasin enriched compositions can be obtained from soybean, wheat, barley, soy isolates, soy concentrates, or other soy derived products, whether or not commercially obtained.

As used herein "digested" refers to the treatment of a polypeptide with a digestive material that breaks it down into its component amino acids. Examples of digestive materials that can be used are well known in the art, and include, without limitation, pancreatin and other proteases such as trypsin, chymotrypsin, pepsin, Proteinase K, thermolysin, thrombin, Arg-C proteinase, Asp-N endopeptidase, AspN endopeptidase+N-terminal Glu, BNPS-Skatole, CNBr, clostripain, formic acid, glutamyl endopeptidase, iodosobenzoic acid, LysC, LysN, NTCB (2-nitro-5-thiocyanobenzoic acid), and Staphylococcal peptidase.

As used herein "partially digested biologically active" in relation to a polypeptide refers to the treatment of a polypeptide with a digestive material under conditions that increase the biological activity of the polypeptide.

The phrase "combination therapy" embraces the administration of a composition of the present invention in conjunction with another pharmaceutical agent that is indicated for treating or preventing a disorder, as part of a specific treatment regimen intended to provide a beneficial effect from the co-action of these therapeutic agents.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

The compositions herein may comprise, consist essentially of, or consist of any of the elements as described herein.

The practice of the present invention will employ, unless otherwise indicated, conventional techniques of molecular biology (including recombinant techniques), microbiology, cell biology, biochemistry, immunology, and protein kinetics, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); and Mass isotopomer distribution analysis at eight years: theoretical, analytic and experimental considerations by Hellerstein and Neese (Am J Physiol 276 (Endocrinol Metab. 39) E1146-E1162, 1999), all of which are incorporated herein by reference in their entirety.

Furthermore, procedures employing commercially available assay kits and reagents will typically be used according to manufacturer-defined protocols unless otherwise noted.

SUMMARY OF THE INVENTION

The present disclosure relates generally to products and methods using lunasin-enriched soy extract (LunaRich X™) combined with Reliv Now © to reduce free fatty acids (FFA) and increase leptin and adiponectin levels in plasma for the control of obesity, type 2 diabetes and metabolic syndrome.

The present invention contemplates a food supplement comprising lunasin enriched soy extract and Pycnogenol® (French maritime pine bark extract). The present invention contemplates that food supplement wherein said lunasin enriched soy extract is present in a concentration of between 1% and 5% by weight. More specifically, the present invention contemplates the food supplement further comprising: soy protein isolate, low fat soy flour, lecithin, minerals, vitamins, calcium carbonate, brewer's yeast, dicalcium phosphate, inulin, L-methionine, kelp, rutin, licorice root, rhubarb root, cayenne pepper, rose hips, butternut bark, Irish moss, bromelain, papain, garlic powder and soy flour enzyme.

The present invention contemplates a method for lowering free fatty acids in an individual in need thereof, comprising administering to an individual a composition comprising: lunasin enriched soy extract and Pycnogenol® (French maritime pine bark extract), and more specifically wherein the composition further comprises: soy protein isolate, low fat soy flour, lecithin, minerals, vitamins, calcium carbonate, brewer's yeast, dicalcium phosphate, inulin, L-methionine, kelp, rutin, licorice root, rhubarb root, cayenne pepper, rose hips, butternut bark, Irish moss, bromelain, papain, garlic powder and soy flour enzyme. In a specific embodiment of the present invention, administering comprises oral ingestion of the composition. In a specific embodiment of the present invention the composition is in the form of a capsule, tablet, powder, semi-solid formulation, liquid, gel, suspension, or aerosol spray. In a specific embodiment of the present invention said lunasin enriched soy extract is present in a concentration of between 1% and 5% by weight.

The present invention contemplates a method for increasing leptin plasma levels in an individual in need thereof, comprising providing to an individual a composition comprising: lunasin enriched soy extract and Pycnogenol® (French maritime pine bark extract), and more specifically wherein the composition further comprises: soy protein isolate, low fat soy flour, lecithin, minerals, vitamins, calcium carbonate, brewer's yeast, dicalcium phosphate, inulin, L-methionine, kelp, rutin, licorice root, rhubarb root, cayenne pepper, rose hips, butternut bark, Irish moss, bromelain, papain, garlic powder and soy flour enzyme. In a specific embodiment of the present invention, administering comprises oral ingestion of the composition. In a specific embodiment of the present invention the composition is in the form of a capsule, tablet, powder, semi-solid formulation, liquid, gel, suspension, or aerosol spray. In a specific embodiment of the present invention said lunasin enriched soy extract is present in a concentration of between 1% and 5% by weight.

The present invention contemplates a method for increasing adiponectin plasma levels in an individual in need thereof, comprising providing to an individual a composition comprising: lunasin enriched soy extract and Pycnogenol® (French maritime pine bark extract), and more specifically wherein the composition further comprises: soy protein isolate, low fat soy flour, lecithin, minerals, vitamins, calcium carbonate, brewer's yeast, dicalcium phosphate, inulin, L-methionine, kelp, rutin, licorice root, rhubarb root, cayenne pepper, rose hips, butternut bark, Irish moss, bromelain, papain, garlic powder and soy flour enzyme. In a specific embodiment of the present invention, administering comprises oral ingestion of the composition. In a specific embodiment of the present invention the composition is in the form of a capsule, tablet, powder, semi-solid formulation, liquid, gel, suspension, or aerosol spray. In a specific embodiment of the present invention said lunasin enriched soy extract is present in a concentration of between 1% and 5% by weight.

The present invention further contemplates a method for treating obesity in an individual in need thereof, comprising providing to an individual a composition comprising: lunasin enriched soy extract, soy protein isolate, low fat soy flour, lecithin, minerals, vitamins, calcium carbonate, brewer's yeast, dicalcium phosphate, inulin, L-methionine, kelp, rutin, licorice root, rhubarb root, cayenne pepper, rose hips, butternut bark, Irish moss, Pycnogenol® (French maritime pine bark extract), bromelain, papain, garlic powder and soy flour enzyme.

DESCRIPTION OF THE FIGURES

The above-mentioned features and objects of the present disclosure will become more apparent with reference to the following description taken in conjunction with the accompanying drawings wherein like reference numerals denote like elements and in which.

GENERAL DESCRIPTION OF THE PREFERRED EMBODIMENTS

Figure 1:
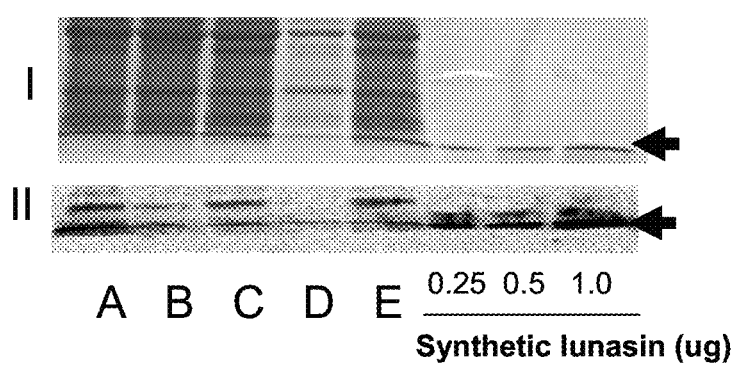
FIG. 1 is a digital image of a Coomasie blue stained SDS-PAGE gel (I) and a photograph of a Western blot analysis (II) showing 20 ug sized samples of soy protein extracted from five different commercial sources of soy protein (A-E) and 0.25 ug, 0.5 ug and 1.0 ug samples of synthetic lunasin. Each 5 kDa lunasin band is indicated by an arrow.

This invention relates generally to products and methods using lunasin-enriched soy extract combined with Reliv Now® to reduce free fatty acid (FFA) levels and increase leptin and adiponectin levels in plasma in individuals for the control of obesity, type 2 diabetes and metabolic syndrome. More specifically, the present invention relates to novel compositions comprising lunasin enriched soy extract and Reliv Now© formulations, methods of using these compositions in individuals for the control of obesity, type 2 diabetes and metabolic syndrome, and methods of making compositions comprising them.

Lunasin is a bioactive component in soy with a novel chromatin-binding property and epigenetic effects on gene expression. See Galvez, A. F. and B. O. de Lumen (1999). "A soybean cDNA encoding a chromatin-binding peptide inhibits mitosis of mammalian cells." *Nat Biotechnol* 17(5): 495-500, and Galvez, A. F., et al. (2001). "Chemopreventive property of a soybean peptide (lunasin) that binds to deacetylated histones and inhibits acetylation." *Cancer Res* 61(20): 7473-7478, both of which are hereby incorporated by reference in their entirety for all purposes.

The soy peptide is heat stable, water soluble and found in significant amounts in select soy protein preparations. See Gonzalez de Mejia, E., et al. (2004). "Lunasin concentration in different soybean genotypes, commercial soy protein, and isoflavone products." *J Aqric Food Chem* 52(19): 5882-5887, hereby incorporated by reference in its entirety for all purposes. It can get inside mammalian epithelial cells through its RGD cell adhesion motif, bind preferentially to deacetylated histones and inhibit histone H3 and H4 acetylation. See Galvez, A. F., et al. (2001) *Cancer Res* 61(20): 7473-7478.

There is growing evidence that responses to dietary and environmental effects involve epigenetic changes in gene expression, which are modulated by the reversible processes of DNA methylation-demethylation and histone acetylation-deacetylation See DePinho, R. A. (1998). "Transcriptional repression. The cancer-chromatin connection." *Nature* 391 (6667): 533, 535-536, and Shahbazian, M. D. and M. Grunstein (2007). "Functions of site-specific histone acetylation and deacetylation." *Annu Rev Biochem* 76: 75-100, both of which are hereby incorporated by reference in their entirety for all purposes.

Lunasin is the first natural substance to be identified as a histone acetylase inhibitor, although it does not directly affect the histone acetylase enzyme. It inhibits H3 and H4 acetylation by binding to specific deacetylated lysine residues in the N-terminal tail of histones H3 and H4, making them unavailable as substrates for histone acetylation.

The elucidation of the mechanism of action makes lunasin an important molecule for research studies to understand the emerging role of epigenetics and chromatin modifications in biological processes that can impact the development of chronic diseases, such as obesity, diabetes and metabolic syndrome.

Lunasin has been shown to bind specifically to Lysine 14 and Lysine 8 of the amino terminal tails of histones H3 and H4, respectively. The binding of lunasin to H3-Lys14 prevents the acetylation of this lysine residue by the PCAF histone acetylase enzyme, and has been shown to reduce the expression of HMG Co-A reductase. Galvez, A. (2012). "identification of lunasin as the active component in soy protein responsible for reducing LDL cholesterol and risk of cardiovascular disease." Circulation Research 126: A10693. The binding of lunasin to H4-Lys8 also inhibits the acetylation of this specific lysine residue by histone acetylase enzymes, p300, HAT1 and PCAF. However, under basal conditions, the binding of lunasin to H4-Lys8 has been shown to increase acetylation of H4-Lysine16, a key modification required for chromatin accessibility and gene activation. Microarray analysis revealed that lunasin upregulates the expression of genes that protect non-malignant prostate cells from tumorigenesis. Galvez, A. F., et al. (2011). "Differential expression of thrombospondin (THBS1) in tumorigenic and nontumorigenic prostate epithelial cells in response to a chromatin-binding soy peptide." Nutr Cancer 63(4): 623-636. The epigenetic effect of lunasin to turn on and off gene expression depending on environmental cues that we have discovered made it amenable to studies to determine its effect in combination with commercially available formulaic compounds.

Lunasin is herein identified as an active component of soy. Compositions and methods of making and using lunasin for, among other things, compositions for the reduction of free fatty acid levels and the increase of leptin levels and adiponectin levels in plasma are also described.

Leptin and adiponectin levels are both implicated in weight reduction and management. Leptin signals the brain when the body had enough food, producing the feeling of satiety (Baicy, K., et al. (2007). "Leptin replacement alters brain response to food cues in genetically leptin-deficient adults." *Proc Natl Acad Sci USA* 104(46): 18276-18279). Like leptin, adiponectin exerts some of its weight reduction via the brain (Nedvidkova, J., et al. (2005). "Adiponectin, an adipocyte-derived protein." *Physiol Res* 54(2): 133-140). The two hormones perform complementary actions and can have additive effects on weight management. Results disclosed herein show that both leptin and adiponectin levels were increased when LES and Reliv Now® were added to the diet and these corresponded to a significantly lower weight gain.

Health Effects of Lowering Free Fatty Acids

Elevated levels of free fatty acids (FFA) have been associated with insulin resistance in obese patients (Boden, G. (2011). "Obesity, insulin resistance and free fatty acids." Curr Opin Endocrinol Diabetes Obes 18(2): 139-143) and can increase inflammation (Tataranni, P. A. and E. Ortega (2005). "A burning question: does an adipokine-induced activation of the immune system mediate the effect of overnutrition on type 2 diabetes?" Diabetes 54(4): 917-927). Insulin resistance and pro-inflammatory response are clinically important because they can lead to several diseases like type 2 diabetes, hypertension and cardiovascular disease. There is a lack of effective treatments to lower plasma free fatty acids (Boden, G. (2011) Curr Opin Endocrinol Diabetes Obes 18(2): 139-143. The discovery that the combination of LES and Reliv Now® leads to the lowering of free fatty acids, provides a novel way of preventing insulin resistance and the associated disease modalities arising from this health condition. Without limiting the invention to a particular mechanism of action, it is speculated that the free fatty acid lowering activity of LES and Reliv Now® can be attributed to the increased plasma levels of leptin and adiponectin that act synergistically to reduce fatty acid by lipolysis (leptin) and by fatty acid oxidation (adiponectin).

Health Effects of Increasing Plasma Adiponectin Levels

Besides the effect of adiponectin in lowering free fatty acid by B-oxidation (Nedvidkova, J., et al. (2005). "Adiponectin, an adipocyte-derived protein." *Physiol Res* 54(2): 133-140), adiponectin has also been shown to increase glucose uptake (Diez, J. J. and P. Iglesias (2003). "The role of the novel adipocyte-derived hormone adiponectin in human disease." *Eur J Endocrinol* 148(3): 293-300), to lower triglyceride (Nedvidkova, J., et al. (2005)), to increase insulin sensitivity (Diez, J. J. and P. Iglesias (2003)), to weight loss (Diez, J. J. and P. Iglesias (2003)) and to control energy metabolism (Vasseur, F., et al. (2006). "Adiponectin, type 2 diabetes and the metabolic syndrome: lessons from human genetic studies." *Expert Rev Mol Med* 8(27): 1-12). Low level of adiponectin is an independent risk factor of developing metabolic syndrome (Renaldi, Pramono et al. 2009) and type 2 diabetes (Lara-Castro, C., et al. (2007). "Adiponectin and the metabolic syndrome: mechanisms mediating risk for metabolic and cardiovascular disease." *Curr Opin Lipidol* 18(3): 263-270). There is no known adiponectin therapy, so the discovery that LES and Reliv Now® can increase endogenous plasma level of adiponectin provides effective treatment to control and prevent obesity, type 2 diabetes, fatty liver disease (Hug, C. and H. F. Lodish (2005). "The role of the adipocyte hormone adiponectin in cardiovascular disease." *Curr Opin Pharmacol* 5(2): 129-134) and may also affect breast cancer (Kaklamani, V. G., et al. (2008). "Variants of the adiponectin and adiponectin receptor 1 genes and breast cancer risk." *Cancer Res* 68(9): 3178-3184.)

Health Effects of Increasing Plasma Leptin Levels

Besides the effect of leptin in lowering free fatty acid by lipolysis (Wang, M. Y., et al. (1999). "Novel form of lipolysis induced by leptin." *J Biol Chem* 274(25): 17541-17544), leptin has been shown to inhibit appetite and increase energy expenditure that lead to weight loss (Keim, N. L., et al. (1998). "Relation between circulating leptin concentrations and appetite during a prolonged, moderate energy deficit in women." *Am J Clin Nutr* 68(4): 794-801) and the improvement of T cell immune response which prevents atherosclerosis (Taleb, S., et al. (2007). "Defective leptin/leptin receptor signaling improves regulatory T cell immune response and protects mice from atherosclerosis." *Arterioscler Thromb Vasc Biol* 27(12): 2691-2698). There are currently no effective treatments to increase leptin levels beyond the injection of recombinant leptin. The discovery that daily supplementation with LES and Reliv Now® can help increase endogenous level of leptin provides an alternative low cost treatment for obesity, type 2 diabetes and the reduction of atherosclerosis and risk for cardiovascular disease.

For Example 4 below, a lunasin enriched soy extract was obtained as follows: soy protein concentrate found to contain biologically active lunasin was used as starting material in a one-step buffer extraction using 0.1×PBS followed by centrifugation to separate the supernatant. Around 2 volumes of acetone was added to supernatant and precipitate was separated by centrifugation with filter bags before vacuum drying to get a lunasin enriched soy extract. In certain embodiments of the present invention, instead of acetone precipitation, a variation to this procedure is to concentrate the supernatant after buffer extraction by heating to 75° C. with vacuum up to $1/10^{th}$ of original volume, followed by freeze drying to get a powder form of lunasin enriched soy extract.

Dosing

In one exemplary embodiment of the present invention, a product containing an effective amount of lunasin enriched soy extract and Reliv Now® that lowers cholesterol levels in an individual that consumes the product is provided. It should be appreciated that the effective amount of the lunasin enriched soy extract and Reliv Now® will depend, at least in part, on the size, weight, health and desired goals of the individuals consuming the compositions.

Depending upon the particular needs of the individual subject involved, the compositions of the present invention can be administered in various doses to provide effective treatment concentrations based upon the teachings of the present invention. Factors such as the activity of the selected compositions, the physiological characteristics of the subject, the extent or nature of the subject's disease or pathological condition, and the method of administration will determine what constitutes an effective amount of the selected compositions. Generally, initial doses will be modified to determine the optimum dosage for treatment of the particular subject. Suitable dosages can be chosen by taking into account any or all of such factors as the size, weight, health, age, and sex of the human or individual, the desired goals of the patient, the severity of the pathological condition for which the composition is being administered, the response to treatment, the type and quantity of other medications being given to the patient that might interact with the composition, either potentiating it or inhibiting it, and other pharmacokinetic considerations such as liver and kidney function. These considerations are well known in the art and are described in standard textbooks.

A therapeutically effective amount of any embodiment of the present invention is determined using methods known to pharmacologists and clinicians having ordinary skill in the art. For example, an effective amount can be determined subjectively by administering increasing amounts of the compositions of the present invention until such time the patient being treated shows reduction in cholesterol, total cholesterol, LDL cholesterol or lipid levels. Blood levels of the composition, cholesterol and lipid levels can be determined using routine biological and chemical assays and these blood levels can be matched to the route of administration. The blood level and route of administration giving the most desirable level of cholesterol reduction can then be used to establish an "effective amount" of the pharmaceutical composition for treatment.

This same method of titrating a composition in parallel with administration route can be used to ascertain a therapeutically effective amount of the compositions of the present invention for treating any and all disorders described herein. In addition, animal models as described below can be used to determine applicable dosages for a particular disease or pathological condition. Typically, dosage-effect relationships from in vitro or in vivo tests initially can provide useful guidance on the proper doses for subject administration.

In one embodiment of the present invention related to reducing plasma levels of free fatty acids, and increasing plasma levels of leptin and adiponectin, methods and compositions of the invention encompass a dose of a composition comprising lunasin enriched soy extract of about 5 mg to 2 grams, preferably 100 mg to 1 g more preferably approximately 500 mg per day.

In at least one preferred embodiment of the present invention the ratio of lunasin enriched soy extract:Reliv Now®, by weight, is between 10:90 and 0.1:99.9, preferably between 5:95 and 1:99, more preferably approximately 3:97 lunasin enriched soy extract:Reliv Now®.

A dose can be administered in one to about four doses per day, or in as many doses per day to elicit a therapeutic effect. The dosage form can be selected to accommodate the desired frequency of administration used to achieve the specified dosage, as well as the route of delivery.

The amount of therapeutic agent necessary to elicit a therapeutic effect can be experimentally determined based on, for example, the absorption rate of the agent into the blood serum, the bioavailability of the agent, and by monitoring the levels of free fatty acids, leptin and/or adiponectin in plasma. Determination of these parameters is well within the skill of the art.

Formulations.

The invention also concerns formulations containing the compositions of the present invention. The products and compositions of the present invention can be used alone or in foods, powders, bars, capsules, shakes and other well known products consumed by individuals.

In one preferred embodiment the compositions of the present invention are together with a dietary suitable excipient, diluent, carrier, or with a food. In a preferred embodiment of the present invention, the formulation is in the form of a pill, tablet, capsule, powder, food bar or similar dosage form.

The formulations may be a variety of kinds, such as nutritional supplements, pharmaceutical preparations, vitamin supplements, food additives or foods supplemented with the specified compositions of the invention, liquid or solid preparations, including drinks, sterile injectable solutions, tablets, coated tablets, capsules, powders, drops, suspensions, or syrups, ointments, lotions, creams pastes, gels, or the like.

The formulations may be packaged in convenient dosage forms, and may also include other active ingredients, and/or may contain conventional excipients, pharmaceutically acceptable carriers and diluents. The inclusion of the compositions of the present invention in herbal remedies and treatments is also a preferred part of the invention.

Some embodiments of the present invention encompass methods for treating one or more of the following diseases or conditions: obesity, type 2 diabetes and metabolic syndrome, comprising treating a patient suffering from one of these diseases or conditions with compositions containing lunasin enriched soy extract and various ingredients from Reliv Now® according to methods of the present invention. Another embodiment of the present invention encompasses methods comprising treating, individuals desiring to maintain a particular plasma level of free fatty acids, leptin or adiponectin with compositions containing lunasin enriched soy extract and various ingredients from Reliv Now® according to methods of the present invention.

While the primary use of the materials of the invention is intended for humans, there may be instances where treatment is desired on domestic or farm animals or in experimental animals. Indeed, one aspect of the invention is the use of experimental animals to confirm the safety and efficacy of the compositions of the invention. Thus, products intended for use in humans may be applied to laboratory animals such as rats, mice or rabbits to confirm the ability of the individual preparation to reduce or control cholesterol levels and to assure that an individual preparation is not toxic. The use of the materials of the invention in the context of quality control, as just described, is part of the invention.

It should be understood that the foregoing discussion, embodiments and examples merely present a detailed description of certain preferred embodiments. It will be apparent to those of ordinary skill in the art that various modifications and equivalents can be made without departing from the spirit and scope of the invention.

The following non-limiting examples are provided to better illustrate the present invention. The examples are not intended to limit the scope of the present invention and they should not be so interpreted. Other procedures and adaptations will be apparent to one of ordinary skill in the art upon views these reaction schemes and the structures of the compositions according to the invention. Such procedures are deemed to be within the scope of the present invention. Amounts are in weight parts or weight percentages unless otherwise indicated. All of the cited patents and publications are incorporated herein by reference.

EXAMPLES

The following examples are provided in order to demonstrate and further illustrate certain preferred embodiments and aspects of the present invention and are not to be construed as limiting the scope thereof.

Example 1

Lunasin can be extracted from commercial sources of soy protein. Lunasin has been found in significant amounts from commercial sources of soy protein (see de Mejia E G, et al, "Lunasin concentration in different soybean genotypes, commercial soy protein and isoflavone products" *J Agric Food Chem* 52: 5882-5887 (2004)) and its homologues from other seed sources such as barley (Jeong, H. J., et al. (2002). "Barley lunasin suppresses ras-induced colony formation and inhibits core histone acetylation in mammalian cells." *J Aqric Food Chem* 50(21): 5903-5908) and wheat (Jeong, H. J., et al. (2007). "The cancer preventive peptide lunasin from wheat inhibits core histone acetylation." *Cancer Lett* 255(1): 42-48). To identify preferred sources for the starting raw material that can be used for lunasin extraction, several commercially available soy protein products were screened for the presence of lunasin.

The procedure used was as follows: approximately 500 mg of soy protein samples (A-E) obtained from different commercial sources (Solae, St. Louis, MO) were dissolved in 50 mL of aqueous phosphate buffer (pH 7.2) by shaking for 1 hour at room temperature. Samples were centrifuged at 2500 rpm for 30 minutes and the aqueous fraction separated and put in separate tubes. Protein concentrations were measured by Bradford assay and around 20 ug of total protein were loaded onto two Bio-Rad Laboratories (Hercules, California) 16% Tris-Tricine gels. One of the SDS-PAGE gels (I) was stained with Coomasie blue and destained before digital imaging. The 5 kDa lunasin band is indicated by arrow. The other (II) is electroblotted onto nitrocellulose membrane and incubated with affinity-purified lunasin polyclonal antibody (Pacific Immunology, (Ramona, California) followed by HRP-conjugated donkey anti-rabbit secondary antibody (Amersham Biosciences, Piscataway, New Jersey). Lunasin immunosignals (indicated by arrow) are detected using the ECL Western blotting kit from Amersham.

The results appear in FIG. 1. It is clear from the photograph that lunasin concentration varies dramatically from source to source. This assay is a useful tool in identifying sources of natural lunasin for use in the compositions and methods of the present invention. The soy concentrate (sample A in FIG. 1) that contained the most lunasin was used as a starting material in a buffer extraction procedure to produce a lunasin enriched soy extract ("LES") in the following examples and the figures they reference.

Example 2

Lunasin enriched soy extract was produced by first identifying commercially available soy protein preparations that contain significant amounts of lunasin by Western blot analysis using lunasin polyclonal antibody, as described above and in U.S. patent application Ser. No. 12/441,384, Example 3. The soy protein concentrate identified to contain the most lunasin was used as starting material in a one-step buffer extraction procedure (0.1×PBS pH 7.2) followed by centrifugation to separate the supernatant. Two volumes of acetone were added to supernatant and precipitate was separated by centrifugation with filter bags before vacuum drying to get the lunasin enriched soy extract.

In the following experiments, soy flour (SF) was added to the starting soy concentrate (at a 30:70 w/w mixture) before buffer extraction with 0.1×PBS pH 7.2 and acetone precipitation to produce lunasin enriched soy extract plus soy flour (LES+SF.)

Figure 2:
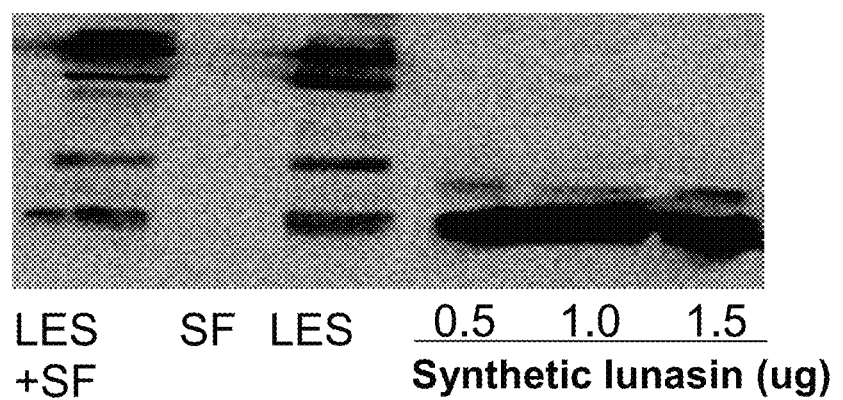
FIG. 2 is a photograph of a Western blot analysis of the protein content, and of particular interest, the lunasin content, of an enriched lunasin soy extract, specifically a formulated lunasin enriched soy extract (LES) soy flour (SF) and LES supplemented with soy flour (LES+SF)

The Western blotting analysis procedure used in this experiment was as follows: approximately 20 ug of total protein from LES, SF and the LES+SF were electrophoresed in 16% Tris-Tricine gels and electroblotted onto nitrocellulose membrane. Blots were incubated with lunasin polylconal antibody followed by HRP-conjugated anti-rabbit secondary antibody before lunasin immunosignals were detected with the ECL kit. Both LES and LES+SF contained significant amounts of lunasin, as shown in FIG. 2.

Example 3

Biological activity of LES (A), LES+SF (B), digested LES+SF (C), digested LES (D), digested soy protein isolate (E) and digested soy concentrate (F) was measured using the H3 histone acetyltransferase (HAT) assay (For more details see U.S. patent application Ser. No. 12/441,384, Example 8.) Around 100 mg total protein of LES, LES+SF, soy protein isolate and soy concentrate were digested by mixing pancreatin (Sigma Life Sciences, Saint Louis, Missouri) at 1:1 (w/w) and incubating for 30 min. at 40° C. To confirm that the HAT assay is working, treatment with synthetic lunasin (+synL) was included. Synthetic lunasin reduced acetylation of histone H3 by the histone acetylase enzyme, PCAF, using core histones isolated from chicken erythrocyte (Upstate/Millipore, Billerica, MA) as template for the HAT assay. Around 10 ug of sample protein was incubated with 1 ug of core histones before undergoing HAT reaction with PCAF enzyme and acetyl CoA substrate. Reaction products were run on 16% Tris-Tricine gels and electroblotted onto nitrocellulose membrane. Blots were incubated with primary antibody raised against acetylated H3 (diacetylated at histone14 and histone10) and HRP-conjugated anti-rabbit secondary antibody before detecting signals using the ECL kit. Low signals indicated that the lunasin peptide was bioactive because it prevented the acetylation of histone H3. Strong signals indicated that the lunasin peptide had been digested and rendered inactive, thus failing to impact levels of histone H3 acetylation. The results are shown in FIG. 3.

There was significant reduction in H3 acetylation in the presence of synthetic lunasin compared to the untreated control. Both the LES (A in FIG. 3) and the LES+SF (B in FIG. 3) were able to significantly reduce H3 acetylation by PCAF, indicating that the lunasin found in both soy protein extracts is biologically active. Pancreatin digestion of LES+

Figure 3:
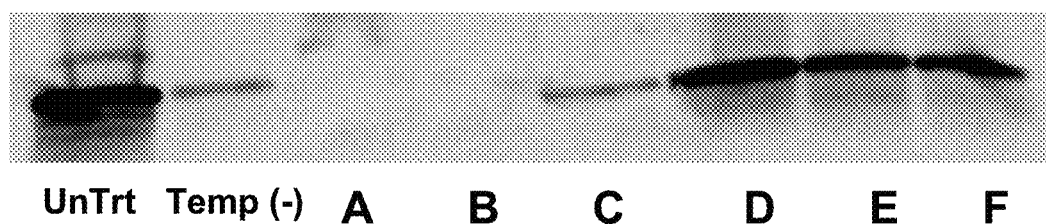
FIG. 3 is a photograph of a Western blot analysis showing the effect of digestion with pancreatin on the biological activity of various extracts, concentrates, and isolates of soy protein. A histone acetyltransferase (HAT) assay was used to determine biological activity. The lanes represent: LES (A), LES+SF (B), digested LES+SF (C), digested LES (D), digested soy protein isolate (E) and digested soy concentrate (F). The core histone from chicken erythrocyte is used as the negative control lane and the template (Temp-) histone for the HAT assay. The positive control lane corresponds to the untreated (Untrt) template core histones in a HAT assay which results in maximum histone acetylation. Low signal indicates that the sample was bioactive because it prevented the acetylation of histone H3. Strong signal indicates that the sample was inactive, thus failing to impact levels of histone H3 acetylation.

SF (C in FIG. 3) reduced the biological activity but not to the extent observed when LES alone is digested (D in FIG. 3). Like LES, soy protein isolate and soy concentrate that contain significant amounts of lunasin, did not show lunasin biological activity after pancreatin digestion (E and F in FIG. 3). These results indicate that the formulated LES+SF protects lunasin to a certain degree from pancreatin digestion, and allows lunasin to retain its biological activity.

Example 4

To determine lunasin bioactivity and levels of bioactive lunasin in different soy preparations we developed a proprietary high-throughput bioassay using an ELISA (enzyme-linked immunosorbent assay)-based protocol. The bioassay uses the ability of lunasin to inhibit histone H3 acetylation by the histone acetylase enzyme, PCAF (p300/CBP associated factor) that specifically acetylates histone H3. The bioassay also measures protein solubility and digestibility which impacts on the level of lunasin bioactivity after digestion.

The Lunasin HAT-ELISA BioAssay Protocol:

Protein is extracted from 500 mg of flour with 0.01×PBS. Two hundred micrograms of protein for each sample is loaded into a 1.5 mL tube and the volume is adjusted using PBS to 200 uL. Pancreatin is added in a 1:1 ratio to the samples and controls. Samples are immediately placed in a 40° C. water bath for digestion at least 10 min, then placed on a heater block for 15 min to boil at 98° C., and flash cooled in an ice water bath for 15 minutes.

The Streptavidin plate is brought to room temperature and washed with 1×TBS. The biotinylated histone H3 peptide is prepared for each sample well. A standard curve using distilled water and biotinylated Acetyl-Histone H3 peptide is prepared. On the Streptavidin plate, 100 uL of the H3 peptide and Ac-H3 standard is loaded into their appropriate wells and the plate is incubated at room temperature for an hour. The plate is washed with 1×TBS and then 100 uL 1×PBS is added to each well. The samples are loaded into their appropriate wells and the plate is incubated 10 minutes at room temperature and then 20 minutes at 30° C. The plate is washed using 1×PBS by hand and blotted dry. The HAT cocktail (Millipore, Billerica, MA USA) is prepared for 50 uL per well. The cocktail is added to sample lanes only and the plate is incubated for 1 hour at 30° C. The plate is washed using 3 times with 1×TBS and then 100 uL of prepared anti-acetyl histone H3 rabbit polyclonal antibody is added to each well. The plate is incubated at room temperature for 1 hour. The plate is washed using 5 times with 1×TBS-T and then 100 uL of prepared goat anti-rabbit antibody with HRP conjugate is added to each well, incubating 30 minutes at room temperature. The plate is washed with 4 times TBS-T, 1 time with 1×TBS and then 100 uL of TMB-ELISA is added. The plate is covered in foil and incubated at room temperature for 15 minutes. The reaction is stopped using 100 uL 2N sulfuric acid and the plate is read at 450 nm with a 570 nm reference filter.

Figure 4:
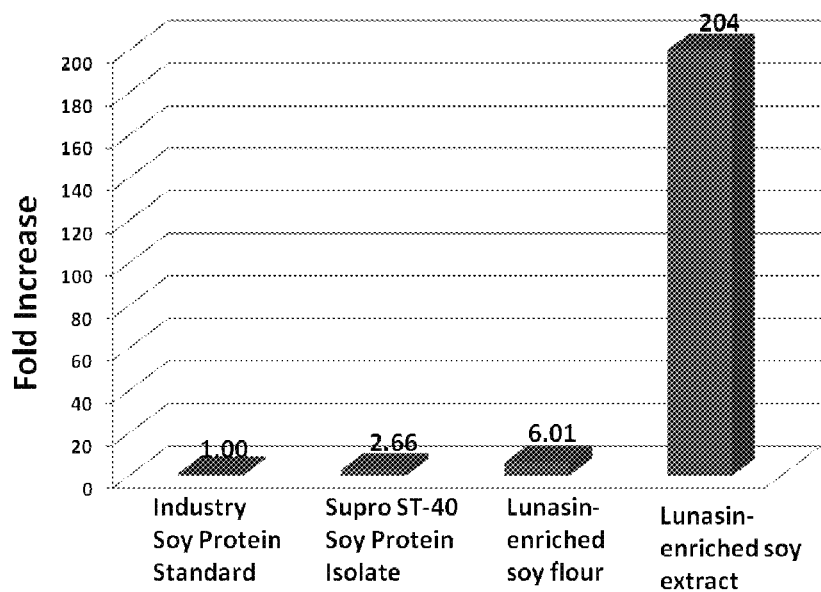
FIG. 4 is a table showing the amounts of bioactive lunasin (relative to the Industry standard soy protein) found in different soy preparations. Numbers indicate the fold increase in bioactive lunasin compared to the industry soy protein standard which is designated 1.00.

Using the lunasin bioassay, we have optimized formulations and dosing of lunasin-enriched soy extracts for use in developing functional food and dietary supplements. FIG. 4 shows the amounts of bioactive lunasin in the different soy protein preparations relative to the industry standard soy protein isolate. The lunasin-enriched soy extract was shown to have approximately 200 fold more bioactive lunasin than the industry soy protein isolate and 100 fold more than the soy protein isolate Supro XT-4o. This means that the amount of bioactive lunasin found in 25 g of Supro XT-40 and 50 g of Industry soy protein standard is equivalent to the amount of bioactive lunasin found in 250 mg of lunasin-enriched soy extract.

Example 5

Reliv Now® is a dietary supplement that is commercially marketed by Reliv™ International (Chesterield, MO) that contains a formulaic compound of soy protein, vitamins, minerals and herbal mixtures. The combination of lunasin-enriched soy extract and Reliv Now® has resulted in the synergistic interaction of lunasin with other bioactive agents found in the Reliv Now® that leads to novel health outcomes. The ingredient list of Reliv Now® and percentages (by weight):

| | |
|---|---|
| 1) Soy protein isolate | 24.9% |
| 2) Low fat soy flour | 32.8% |
| 3) Lecithin | 1.6% |
| 4) Universal Premix (available from Reliv Now ®) | 20.5% |
| 5) Calcium carbonate | 6.8% |
| 6) Brewer's yeast | 3.9% |
| 7) Dicalcium phosphate | 3.6% |
| 8) Inulin | 1.6% |
| 9) Fructose | 1.7% |
| 10) Vanilla flavor | 1.1% |
| 11) Rebiana | 0.05% |
| 12) L-Methionine | 0.21% |
| 13) Kelp | 0.16% |
| 14) Rutin | 0.13% |
| 15) Licorice root | 0.09% |
| 16) Rhubarb root | 0.09% |
| 17) Cayenne pepper | 0.09% |
| 18) Rose Hips | 0.09% |
| 19) Butternut bark | 0.03% |
| 20) Irish Moss | 0.03% |
| 21) Pycnogenol ® | 0.03% |
| 22) Bromelain | 0.02% |
| 23) Papain | 0.02% |
| 24) Garlic powder | 0.02% |
| 25) Soy flour enzyme | 0.03% |

To test the effects of the lunasin-enriched soy extract (LES) in combination with Reliv Now®, we conducted a feeding study using a pig model whose standard casein diet (BV233) were supplemented with 18 g of Reliv Now® (obtained from Reliv Inc. Chesterfield MO) and 500 mgs of lunasin enriched soy extract (obtained from Soy Labs, LLC. Mexico, MO). We chose the Rapacz pig model to test the LES extract because their weight and liver function and morphology are closer to humans than any other animal models. Also, the pigs have mutations to their LDL receptor gene that predispose them to high cholesterol, obesity and increased risk for heart disease (Hasler-Rapacz, Ellegren et al. 1998). The pigs were approximately 1.5 years old and considered obese, weighing more than 20% from normal. The experiment was done at the Veterinary hospital at the University of Missouri, Columbia, MO.

In order to administer Reliv Now®, the 13 g powder was mixed with 10 cc of water and formed into a dough ball that the pigs ate happily. The 500 mg of LES were put into two capsules of 250 mgs each and was fed to the pigs by inserting them into a snack bar that the pigs like to eat. The pigs were maintained on a soy-free diet (BV233 pig chow) throughout the treatment. Pigs were fed their regular diet (BV233) once per day in the morning at approximately 9:00 AM. Later in the afternoon, at approximately 4:00 PM, the Reliv Now® and LES treatments were administered. Weight and blood draws were taken at pre-treatment (0), at 4 weeks, 6 weeks and 8 weeks after treatment has begun. At the end of 8 weeks, there was an additional 4 weeks washout period without treatment and weight and blood draws were also taken at the end of washout period (12 weeks). Blood draws were taken after an overnight fast (approximately 15 h). Blood samples were tested for lipid panel including plasma levels of free fatty acids by the Analytical Laboratory at the Veterinary School of the University of Missouri. Blood samples were collected into monoject tubes with 15% EDTA, centrifuged for 20 min @ 3300 rpm to separate the blood plasma, which were transferred to 1 ml cryogenic vials and stored at −70° C. to test for leptin and adiponectin levels. Plasma levels of leptin and adiponectin were determined using porcine leptin and adiponectin ELISA kits obtained from USCN Life Sciences, Inc. (Houston, TX USA). Standard protocols from the manufacturer were followed, including the use of 3 replicate measurements for each data point, to detect and quantify the amounts of leptin and adiponectin in the plasma.

Results of the Pig Feeding Experiment

Figure 5:
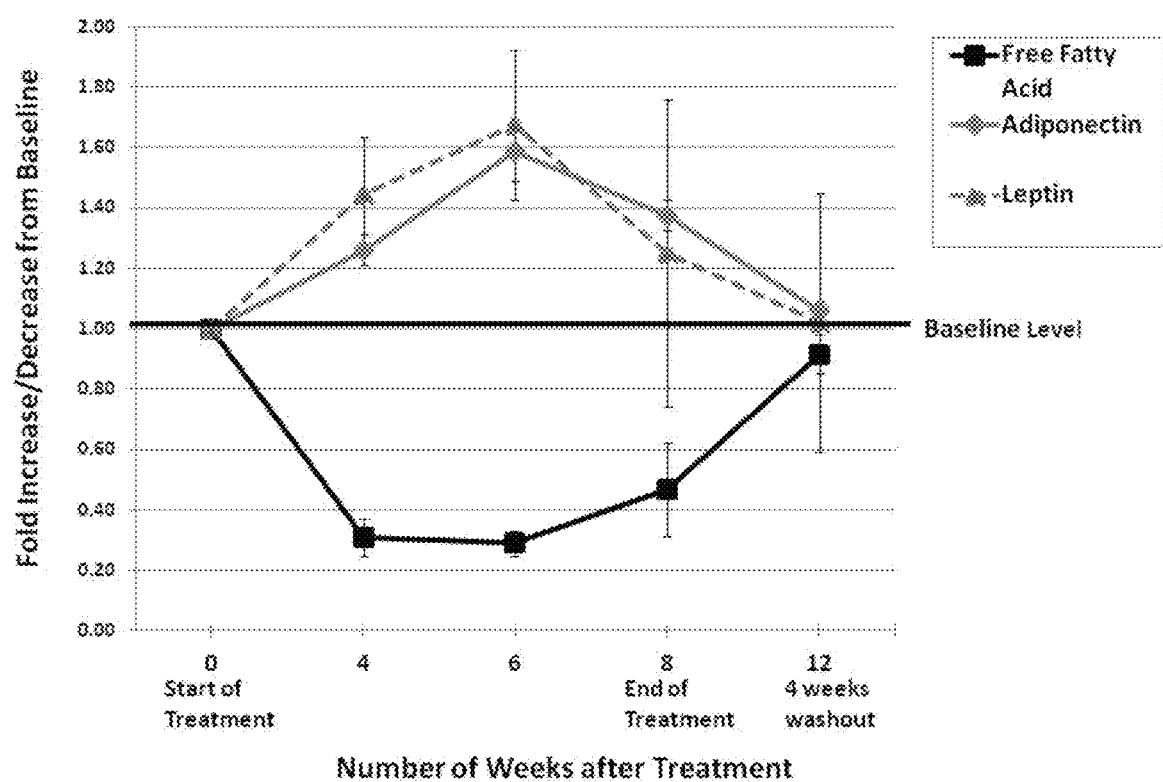
FIG. 5 is a graph showing the effect of Lunasin-enriched soy extract (LES) and Reliv Now® daily supplementation on plasma free fatty acid (FFA), adiponectin (Adp) and leptin (Lep) levels in 5 Rapacz pigs with disposition to heart disease and obesity. The mean values from 5 pigs and their standard error were standardized using the pre-treatment values (0 weeks) of FFA, Adp and Lep as baseline levels. Values above the standard baseline level of 1.0 indicate increased levels of Adp and Lep, and below baseline level indicate decreased levels of FFA.

The standard diet of the 5 Rapacz pigs used in the experiment was a soy-free, casein-based pig chow (BV233). The amount of plasma free fatty acid before the start of treatment (Time 0) was used as the baseline level. Daily treatment with 500 mgs of LES and 18 g Reliv Now® formulaic compound resulted in the significant reduction of free fatty acid (FFA) from the baseline level (FIG. 5). The FFA levels at 4, 6 and 8 weeks of treatment were all significantly lower than the pre-treatment levels of FFA. When treatment ended after 8 weeks and the pigs were fed only the standard casein diet, the FFA levels went back up close to the baseline level after 4 weeks of washout (Time: 12 weeks) (FIG. 5). These results indicate that the supplementation of the standard casein diet with 500 mgs LES and 18 g of Reliv Now® causes the significant reduction in plasma free fatty acid levels and when supplementation is stopped, the FFA level goes back up to pre-treatment, baseline level.

To determine the mechanism of action involved in the reduction of FFA, the levels of leptin and adiponectin, two adipocyte hormones involved in FFA catabolism and oxidation, were measured in the blood plasma. The adiponectin levels increased significantly after 4 weeks (20% increase), 6 weeks (60%) and 8 weeks (40%) of treatment from baseline level (FIG. 5). At 4 weeks washout (T=12 weeks), plasma adiponectin went back down to baseline level (FIG. 5). This result is inverse that of free fatty acid, indicating that the effect of the treatment with LES and Reliv Now® on reduced levels of free fatty acid can be explained by the increased amounts of adiponectin in the plasma which is important in fatty acid oxidation (Diez and Iglesias 2003).

Leptin is another adipocyte hormone involved in lipolysis that can reduce free fatty acid levels. Leptin levels in the blood plasma of pigs after 4 and 6 weeks of treatment with LES and Reliv Now® were significantly increased by 52% and 64%, respectively from baseline levels, although there is a wide variation. The mean leptin level after 8 weeks of treatment was higher than baseline level but because of the wide variation in values among the 5 pigs, it was not significantly different from baseline. At 12 weeks (after 4 weeks washout), the leptin levels have gone down to baseline level, similar to the results obtained with adiponectin and FFA. The increase in leptin level after 4 and 6 weeks and to a lesser extent 8 weeks of treatment can also explain the reduced levels of FFA. The similar trend of ADP and Lep upon treatment with LES and Reliv Now®, suggest that they may be acting synergistically to reduce FFA levels in the plasma.

Figure 6:
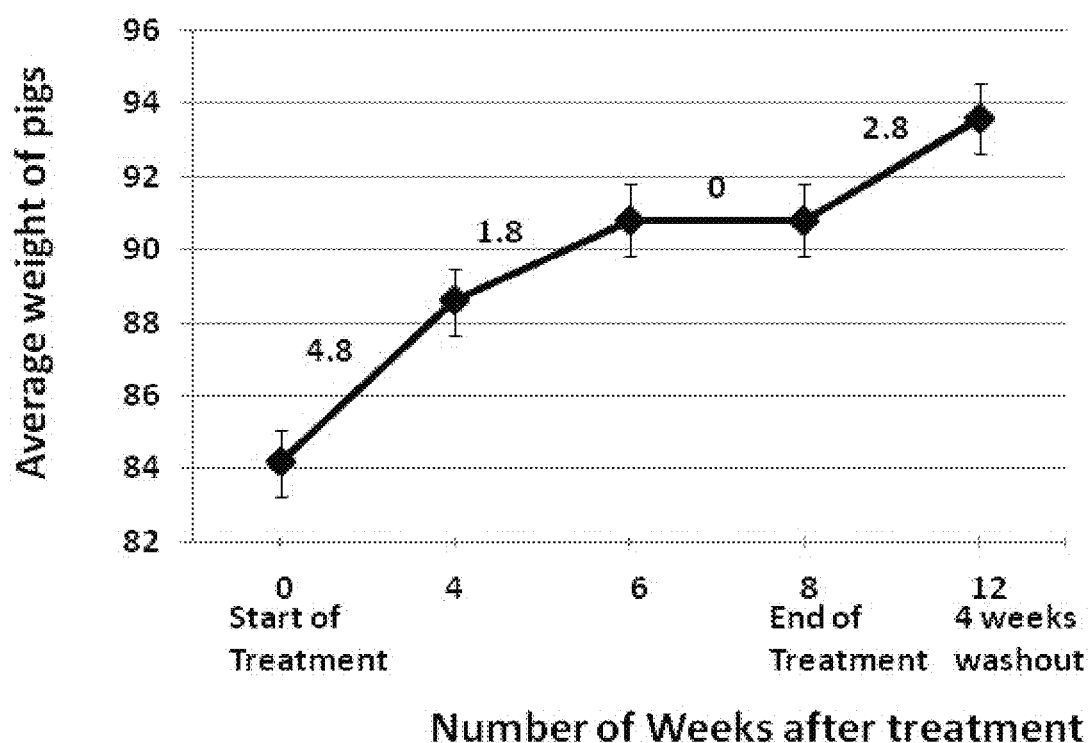
FIG. 6 is a graph showing the effect of Lunasin-enriched Soy extract (LES) and Reliv Now® daily supplementation on the average weight of 5 Rapacz pigs. Numbers in between time points indicate average range of weight gain of the 5 pigs.

FFA levels are elevated in most obese subjects and are directly correlated with weight (Baicy, London et al. 2007) (Boden, 2011). To determine whether the reduced FFA levels in the pigs, upon treatment with LES and Reliv Now®, had any effect on weight, we determined the average weight of the pigs at each time point and measured the weight gain in between each time point. Results shown in FIG. 6 show that the pigs did not gain any weight at the time point between 6 weeks and 8 weeks when the FFA levels were at its lowest. FIG. 6 is a graph showing the effect of Lunasin-enriched Soy extract (LES) and Reliv Now® daily supplementation on the average weight of 5 Rapacz pigs. Numbers in between timepoints indicate average range of weight gain of the 5 pigs. See Tataranni, P. A. and E. Ortega (2005). "A burning question: does an adipokine-induced activation of the immune system mediate the effect of overnutrition on type 2 diabetes?" Diabetes 54(4): 917-927. The highest gain in weight (4.8 kg.) occurred at 0 to 4 weeks of treatment, when FFA levels were still high at baseline levels. Between 4 weeks and 8 weeks, gain weight was at 1.8 kg which corresponds to low levels of FFA. At 4 weeks after washout (T=12 weeks), pigs gained 2.8 kgs which corresponds to the increase of FFA to baseline levels. These results indicate that the reduction of FFA due to treatment with LES and Reliv Now® led to a corresponding reduction in weight gain of the pigs.

Results of the experiment show that both leptin and adiponectin levels were increased when LES and Reliv Now® were added to the diet and these corresponded to a significantly lower weight gain.

The above specification, examples and data provide a complete description of the manufacture and use of the compositions of the invention. While the products, compositions and related methods have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims. All the patents, journal articles and other documents discussed or cited above are herein incorporated by reference. All the patents, journal articles and other documents discussed or cited herein or listed below are herein incorporated by reference.

The invention claimed is:

1. A method for increasing leptin plasma levels in an individual in need thereof, comprising administering to the individual a composition comprising: lunasin enriched soy extract and French maritime pine bark extract.

2. The method of claim 1, wherein the composition further comprises: soy protein isolate, soy flour, lecithin, minerals, vitamins, calcium carbonate, brewer's yeast, dicalcium phosphate, inulin, L-methionine, kelp, rutin, licorice root, rhubarb root, cayenne pepper, rose hips, butternut bark, Irish moss, bromelain, papain, garlic powder and soy flour enzyme.

3. The method of claim 1 wherein administering comprises oral ingestion of the composition.

4. The method of claim 1, wherein said composition comprises a capsule, tablet, powder, semi-solid formulation, liquid, gel, suspension, or aerosol spray.

5. The method of claim 1, wherein said individual suffers from obesity.

6. The method of claim 4, wherein said lunasin enriched soy extract is present in a concentration of between 1% and 5% by weight.

7. The method of claim 4, wherein said composition is administered on a daily basis.

8. The method of claim 4, wherein said composition comprises between 5 mg and 2 grams of lunasin enriched soy extract.

9. The method of claim 4, wherein said composition comprises between 100 mg and 1 gram of lunasin enriched soy extract.

10. The method of claim 4, wherein said composition comprises approximately 500 mg of lunasin enriched soy extract.

11. A method for increasing leptin plasma levels in an individual in need thereof, comprising administering to the individual a composition comprising: a) lunasin enriched soy extract at a concentration of between 1% and 5% by weight, and b) French maritime pine bark extract.

12. The method of claim 11, wherein the individual suffers from obesity.

13. The method of claim 11, wherein the composition further comprises: soy protein isolate, soy flour, lecithin, minerals, vitamins, calcium carbonate, brewer's yeast, dicalcium phosphate, inulin, L-methionine, kelp, rutin, licorice root, rhubarb root, cayenne pepper, rose hips, butternut bark, Irish moss, bromelain, papain, garlic powder and soy flour enzyme.

14. The method of claim 11, wherein administering comprises oral ingestion of the composition.

15. The method of claim 11, wherein composition is in the form of a capsule, tablet, powder, semi-solid formulation, liquid, gel, suspension, or aerosol spray.

16. The method of claim 11, wherein said composition is administered on a daily basis.

17. A method for increasing leptin levels in an individual in need thereof, comprising administering to the individual a composition comprising: lunasin enriched soy extract, soy protein isolate, soy flour, lecithin, minerals, vitamins, calcium carbonate, brewer's yeast, dicalcium phosphate, inulin, L-methionine, kelp, rutin, licorice root, rhubarb root, cayenne pepper, rose hips, butternut bark, Irish moss, French maritime pine bark extract, bromelain, papain, garlic powder and soy flour enzyme.

18. The method of claim 17, wherein the individual suffers from obesity.

19. The method of claim 17, wherein said lunasin enriched soy extract is present in a concentration of between 1% and 5% by weight.

20. The method of claim 17, wherein administering comprises oral ingestion of the composition.

21. The method of claim 17, wherein said composition is in the form of a capsule, tablet, powder, semi-solid formulation, liquid, gel, suspension, or aerosol spray.

* * * * *